(12) United States Patent
Taylor et al.

(10) Patent No.: US 8,455,188 B2
(45) Date of Patent: Jun. 4, 2013

(54) MODIFICATION OF EXOSOMAL COMPONENTS FOR USE AS A VACCINE

(75) Inventors: Douglas D. Taylor, Louisville, KY (US); Cicek Gercel-Taylor, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 416 days.

(21) Appl. No.: 12/524,432

(22) PCT Filed: Jan. 28, 2008

(86) PCT No.: PCT/US2008/052205
§ 371 (c)(1),
(2), (4) Date: Jul. 24, 2009

(87) PCT Pub. No.: WO2008/092153
PCT Pub. Date: Jul. 31, 2008

(65) Prior Publication Data
US 2010/0092524 A1    Apr. 15, 2010

Related U.S. Application Data

(60) Provisional application No. 60/897,645, filed on Jan. 26, 2007.

(51) Int. Cl.
*C12Q 1/68* (2006.01)
(52) U.S. Cl.
USPC ........ 435/6.1; 536/24.5; 536/24.31; 536/24.1
(58) Field of Classification Search
None
See application file for complete search history.

(56) References Cited

U.S. PATENT DOCUMENTS

| | | | |
|---|---|---|---|
| 5,612,030 | A | 3/1997 | Chatterjee et al. |
| 6,136,306 | A | 10/2000 | Granger |
| 6,203,787 | B1 | 3/2001 | Thompson et al. |
| 6,207,147 | B1 | 3/2001 | Hiserodt et al. |
| 6,235,280 | B1 | 5/2001 | Chatterjee et al. |
| 6,277,368 | B1 | 8/2001 | Hiserodt et al. |
| 6,685,911 | B1 | 2/2004 | Zitvogel et al. |
| 6,812,023 | B1 | 11/2004 | Lamparski et al. |
| 6,899,863 | B1 | 5/2005 | Dhellin et al. |
| 7,897,356 | B2 * | 3/2011 | Klass et al. ............... 435/7.1 |
| 2004/0197314 | A1 | 10/2004 | Delcayre et al. |
| 2006/0116321 | A1 | 6/2006 | Robbins et al. |
| 2006/0222654 | A1 | 10/2006 | Delcayre et al. |
| 2006/0233750 | A1 | 10/2006 | Xiang et al. |
| 2008/0268429 | A1 * | 10/2008 | Pietrzkowski ............ 435/6 |

FOREIGN PATENT DOCUMENTS

| | | |
|---|---|---|
| AU | 2004203482 | 8/2004 |
| WO | 9705900 | 2/1997 |
| WO | 0028001 | 5/2000 |
| WO | 2005121369 | 12/2005 |
| WO | 2009036236 | 3/2009 |

OTHER PUBLICATIONS

Kim et al. Clinical Cancer Research 2005, 1010-1020.*
Ahlers et al., "A push-pull approach to maximize vaccine efficacy: abrogating suppression with an IL-13 inhibitor while augmenting help with granulocyte/macrophage colony-stimulating factor and CD40L," Proc. Nat. Acad. Sci. USA, 99, 2002, p. 13020.
Banchereau et al., "Immune and clinical responses in patients with metastatic melanoma to CD34(+) progenitor-derived dendritic cell vaccine," Cancer Res, 61, 2001, p. 6451.
Bass BL, "RNA interference. The short answer," Nature, 411, 2001, pp. 428-429.
Bazzett et al., "Modulation of proliferation and chemosensitivity by procathepsin D in ovarian cancer," Gynecologic Oncology, 74(2), 1999, pp. 181-187.
Belyakov et al., "Mucosal vaccination overcomes the barrier to recombinant vaccinia immunization caused by preexisting poxvirus immunity," Proc. Natl. Acad. Sci. USA, 96(8), 1999, pp. 4512-4517.
Bernstein et al., "Role for a bidentate ribonuclease in the initiation step of RNA interference," Nature, 409(6818), 2001, pp. 363-366.
Berzofsky et al., "Progress on new vaccine strategies for the immunotherapy and prevention of cancer," J. Clin. Invest, 113(11), 2004, pp. 1515-1525.
Berzofsky et al., "Strategies for designing and optimizing new generation vaccines," Nat. Rev. Immunol., 1(3), 2001, pp. 209-219.
Chinni et al., "Humoral Immune Responses to Cathepsin D and Glucose-regulated Protein 78 in Ovarian Cancer Patients," Clin Cancer Res, 3, 1997, pp. 1557-1564.
Delcayre et al., "Exosomes as novel Therapeutic Nanodevices," Current Opinion in Molecular Therapeutics, 2006.
Delcayre et al., "Exosome Display Technology: Applications to the Development of New Diagnostics and Therapeutics," Blood Cells, Molecules, and Diseases, 2005.
Delcayre et al., "Dendritic cell-derived exosomes in cancer immunotherapy: exploiting nature's antigen delivery pathway," Future Drugs Ltd.; Expert Rev. Anticancer Ther. 5(3), 2005.

(Continued)

*Primary Examiner* — Kimberly Chong
(74) *Attorney, Agent, or Firm* — Stites & Harbison PLLC; Mandy Wilson Decker

(57) ABSTRACT

The presently disclosed subject matter provides modified cell-derived exosomes substantially lacking one or more immunosuppressive polypeptides. The presently-disclosed subject matter further provides methods of producing the modified exosomes and methods of using the modified exosomes for treating cancers.

24 Claims, 2 Drawing Sheets

OTHER PUBLICATIONS

Duch et al., "Volatile anesthetics significantly suppress central and peripheral mammalian sodium channels," Toxicol. Lett., 100-101, 1998, pp. 255-263.
Elbashir et al., "Duplexes of 21-nucleotide RNAs mediate RNA interference in cultured mammalian cells," Nature, 411(6836), 2001, pp. 494-498.
Elbashir et al., "RNA interference is mediated by 21- and 22-nucleotide RNAs," Genes Dev., 5, 2001, pp. 188-200.
Fire et al., "Potent and specific genetic interference by double-stranded RNA in Caenorhabditis elegans," Nature, 391, 1998, pp. 806-811.
Fire A, "RNA-triggered gene silencing," Trends Genet, 15(9), 1999, pp. 358-363.
Fong et al., "Dendritic cells in cancer immunotherapy," Annu. Rev. Immunol., 18, 2000, pp. 245-273.
Fong et al., "Dendritic cell-based xenoantigen vaccination for prostate cancer immunotherapy," J. Immunol., 167(12), 2001, pp. 7150-7156.
Gibb et al., "Apoptosis as a measure of chemosensitivity to cisplatin and Taxol therapy in ovarian cancer cell lines," Gynecologic Oncology, 65, 1997, pp. 13-22.
Hammond et al., "An RNA-directed nuclease mediates post-transcriptional gene silencing in *Drosophila* cells," Nature, (6775), 2000, pp. 293-296.
Hege et al., "Lung cancer vaccines and gene therapy," Lung Cancer, 41: Suppl, 2003, pp. S103-S113.
Heiser et al., Induction of Polyclonal prostate cancer-specific CTL using dendritic cells transfected with amplified tumor RNA., J. Immunol., 166(5), 2001, pp. 2953-2960.
Huang et al., "A novel antitumor approach: SEA-anchored tumor cells expressing heat shock protein 70 onto the surface elicit strong antitumor efficacy," Immunol Lett, 101, 2005, pp. 71-80.
Jaffee et al., "Novel allogeneic granulocyte-macrophage colony-stimulating factor-secreting tumor vaccine for pancreatic cancer: a phase I trial of safety and immune activation," J. Clin. Oncol., 19(1), 2001, pp. 145-156.
Klinman et al., "CpG motifs present in bacteria DNA rapidly induce lymphocytes to secrete interleukin 6, interleukin 12, and interferon gamma," Proc. Natl. Acad. Sci., USA, 93(7), 1996, pp. 2879-2883.
Koyanagi et al., "Long-term exposure to superantigen induces p27Kip1 and Bcl-2 expression in effector memory CD4+ T cells," Cellular Immunology, 248(2), 2007, pp. 77-85.
Luketic et al., "Antigen Presentation by Exosomes Released from Peptide-Pulsed Dendritic Cells Is not Suppressed by the Presence of Active CTL," J. Immunology, 179(8), 2007, pp. 5424-5432.
Makhija et al., "Regulation of chemotherapy induced apoptosis in ovarian cancer cell spheroids," International Journal of Oncology, 14, 1999, pp. 515-521.
Marshall et al., "Phase I study in advanced cancer patients of a diversified prime- and-boost vaccination protocol using recombinant vaccinia virus and recombinant nonreplicating avipox virus to elicit anti-carcinoembryonic antigen immune responses," J. Clin. Oncol., 18(23), 2002, pp. 3964-3973.
McHugh et al., "Protein transfer of glycosyl-phosphatidylinositol-B7-1 into tumor cell membranes: a novel approach to tumor immunotherapy," Cancer Res, 59, 1999, pp. 2433-2437.
Milazzo et al., "Induction of myeloma-specific cytotoxic T cells using dendritic cells transfected with tumor-derived RNA," Blood 101, (3), 2003, pp. 977-982. Epub Sep. 19, 2002.
Nagarajan et al., "Glycolipid-anchored IL-12 expressed on tumor cell surface induces antitumor immune response," Cancer Res, 62, 2002, pp. 2869-2874.
Nair et al., "Antigen-presenting cells pulsed with unfractionated tumor-derived peptides are potent tumor vaccines," Eur. J. Immunol., 27(3), 1997, pp. 589-597.
Nestle et al., "Vaccination of melanoma patients with peptide- or tumor lysate-pulsed dendritic cells," Nat. Med., 4(3), 1998, pp. 328-332.
Nykanen et al., "ATP requirements and small interfering RNA structure in the RNA interference pathway," Cell, 107 (3), 2001, pp. 309-321.

Ohtsuka et al., "An alternative approach to deoxyoligonucleotides as hybridization probes by insertion of deoxyinosine at ambiguous codon positions," J Biol Chem, 260(5), 1985, pp. 2605 2608.
Rosenberg et al., "Immunologic and therapeutic evaluation of a synthetic peptide vaccine for the treatment of patients with metastatic melanoma," Nat. Med., 4(3), 1998, pp. 321-327.
Rossolini et al., "Use of deoxyinosine-containing primers vs degenerate primers for polymerase chain reaction based on ambiguous sequence information," Mol Cell Probes, 8(2), 1994, pp. 91 98.
Salgia et al., "Vaccination with irradiated autologous tumor cells engineered to secrete granulocyte-macrophage colony-stimulating factor augments antitumor immunity in some patients with metastatic non-small-cell lung carcinoma," J. Clin. Oncol., 21(4), 2003, pp. 624-630.
Sallusto et al., "Efficient presentation of soluble antigen by cultured human dendritic cells is maintained by granulocyte/macrophage colony-stimulating factor plus interleukin 4 and downregulated by tumor necrosis factor alpha," J. Exp. Med., 179(4), 1994, pp. 1109-1118.
Schuler et al., "The use of dendritic cells in cancer immunotherapy," Curr. Opin. Immunol., 15(2), 2003, pp. 138-147.
Simons et al., "Induction of immunity to prostate cancer antigens: results of a clinical trial of vaccination with irradiated autologous prostate tumor cells engineered to secrete granulocyte-macrophage colony-stimulating factor using ex vivo gene transfer," Cancer Res., 59(20), 1999, pp. 5160-5168.
Singh et al., "GENBANK® Accession Nos. AY291443 to AY291450. Comparative structural analysis of staphylococcal enterotoxins A and E, " J Biol Chem, 264, 1989, pp. 4404-4411.
Soiffer et al., "Vaccination with irradiated autologous melanoma cells engineered to secrete human granulocyte-macrophage colony-stimulating factor generates potent antitumor immunity in patients with metastatic melanoma," Proc. Natl. Acad. Sci. USA, 95(22), 1998, pp. 13141-13146.
Su et al., "Immunological and clinical responses in metastatic renal cancer patients vaccinated with tumor RNA-transfected dendritic cells," Cancer Res., 63(9), 2003, pp. 2127-2133.
Taylor et al., "Tumour-derived exosomes and their role in cancer-associated T-cell signaling defects," British Journal of Cancer, 92(2), 2005, pp. 305-311.
Thurner et al., "Vaccination with mage-3A1 peptide-pulsed mature, monocyte-derived dendritic cells expands specific cytotoxic T cells and induces regression of some metastases in advanced stage IV melanoma," J. Exp. Med., 190(11), 1999, pp. 16169-16178.
Tritto et al., "The acquired immune response to the mucosal adjuvant LTK63 imprints the mouse lung with a protective signature," Journal of Immunology, 179(8), 2007, pp. 5346-5357.
Wianny et al., "Specific interference with gene function by double-stranded RNA in early mouse development," Nature Cell Biol, 2(2), 2002, pp. 70-75.
Taylor et al., "Identification of antigenic components recognized by membrane-bound antibodies from ovarian cancer patients," American Journal of Reproductive Immunology, vol. 6, No. 4, Dec. 1, 1984, pp. 179-184, Munksgaard International Publishers, Copenhagen, DK.
Palacio et al., Anti-endometrial autoantibodies in women with a diagnosis of infertility, American Journal of Reproductive Immunology, vol. 38, Nr. 2, Aug. 1997, pp. 100-105.
Draghici Sorin et al., "Epitomics: Serum Screening for the Early Detection of Cancer on Microarrays Using Complex Panels of Tumor Antigens," Expert Review of Molecular Diagnostics, vol. 5, No. 5, 2005, pp. 735-743.
Taylor et al., "Shed Membrane Fragment-Associated Markers for Endometrial and Ovarian Cancers," Gynecologic Oncology, vol. 84, No. 3, 2002, pp. 443-448.
Taylor et al., "Tumour-derived Exosomes and Their Role in Cancer-Associated T-cell Signalling Defects," British Journal of Cancer, vol. 92, No. 2, 2005, pp. 305-311.
Taylor et al., "Pregnancy-Associated Exosomes and Their Modulation of T Cell Signaling," Journal of Immunology, American Association of Immunologists, US, vol. 176, No. 3, 2006, pp. 1534-1542.

Taylor et al., "Patient-Derived Tumor-Reactive Antibodies as Diagnostic Markers for Ovarian Cancer," Gynecologic Oncology, vol. 115, No. 1, 2009, pp. 112-120, Academic Press, London, GB.

Bohler et al., "Endometriosis Markers: 1-20 Immunologic Alterations as Diagnostic Indicators for Endometriosis," Reproductive Sciences, vol. 14(6), 2007, pp. 595-604, Sage Publications, Inc., US.

Taylor et al., "Characterization of Humoral Responses of Ovarian Cancer Patients: Antibody Subclasses and Antigenic Components," Gynecologic Oncology, vol. 116(2), 2010, pp. 213-221, Academic Press, London, GB.

EPO, Supplementary European Search Report for corresponding European Patent Application No. EP 08728418, completed May 20, 2010, The Hague, NL.

Kahlil, A., "Biomarker discovery: A proteomic approach for brain cancer profiling", Cancer Sci., 2007, 98(2), pp. 201-213.

Millimaggi, et al., "Tumor Vesicle-Associated CD147 Modulates the Angiogenic Capability of Endothelial Cells 1", Neoplasia, 2007, 9(4), pp. 349-357.

Piccin et al., "Circulating microparticles: pathophysiology and clinical implications", Elsevier Health, 2007, 21, pp. 157-171.

Schiera et al., "Neurons produce FGF2 and VEGF and secrete them at least in part by shedding extracellular vesicles", J. Cell Mol. Med., 2007, 11(6), pp. 1384-1394.

Zhou et al., "Induction of CML28-specific cytotoxic T cell responses using co-transfected dendritic cells with CML28 DNA vaccine and SOCS1 small interfering RNA expression vector," Biochemical and Biophysical Reserach Communications, Aug. 18, 2006, vol. 347, No. 1, pp. 200-207.

* cited by examiner

MODIFICATION OF EXOSOMAL COMPONENTS FOR USE AS A VACCINE

RELATED APPLICATIONS

The presently disclosed subject matter claims the benefit of U.S. Provisional Patent Application Ser. No. 60/897,645, filed Jan. 26, 2007; the disclosure of which is incorporated herein by reference in its entirety.

GOVERNMENT INTEREST

This presently disclosed subject matter was made in part with U.S. Government support under Grant No. HD042674 awarded by National Institute for Child Health and Health Development (NIH). Thus, the U.S. Government has certain rights in the presently disclosed subject matter.

TECHNICAL FIELD

The presently disclosed subject matter relates to modified exosomes for use as vaccines. In particular, the presently disclosed subject matter relates to utilizing cell-produced exosomes modified to substantially lack one or more immunosuppressive polypeptides and methods of producing and using the exosomes as vaccines and treatments for disorders, including cancers.

BACKGROUND

Cancer is the second leading cause of death in the United States (U.S.). In 1999 there were an estimated 563,100 cancer deaths and each year about 1,222,000 new cancer cases are diagnosed. Among these, solid tumor cancers such as lung, breast, prostate and colorectal cancers are the most common. For example, ovarian cancer remains the fourth leading cause of cancer-related deaths in women, resulting in more than 26,700 new cases and 14,800 deaths annually in the U.S.

Despite encouraging initial antitumor responses, conventional cytotoxic chemotherapy fails to cure the majority of patients with advanced stage ovarian cancer. With the emergence of drug resistance in refractory tumors, immunologic treatment strategies have been explored.

Monoclonal antibodies have been developed for specific cancer types. HERCEPTIN® (Trastuzumab), RITUXAN® (rituximab), and CAMPATH® (alemtuzumab) have been a clinical and commercial success. But these medicines provide only passive treatment without recruiting constructive participation by the host's immune system. They also leave out what may be the most powerful immune effector mechanism for causing tumor regression: the cytotoxic T lymphocyte (CTL) compartment.

Considerable effort is underway in laboratories all over the world to find an active vaccine that will overcome the natural tolerance to self-antigens, and induce a strong anti-tumor response.

Peptide vaccines have been developed based on tumor associated antigens like carcinoembryonic antigen (CEA) or gp100, sometimes with epitope enhancement to enhance immunogenicity (S. A. Rosenberg et al., Nat. Med. 4:321, 1998). Cytokines, chemokines, or costimulatory molecules have been used as potential adjuvants (J. A Berzofsky et al., Nat. Rev. Immunol. 1:209, 2001; J. D. Ahlers et al., Proc. Nat. Acad. Sci. USA 99:13020, 2002). Active immune response to tumor antigen has also been achieved in cancer patients using anti-idiotype antibody, made to mimic the target antigen while providing further immunogenicity (U.S. Pat. Nos. 5,612,030 and 6,235,280). Nucleic acid vectors based on adenovirus, vaccinia, and avipox encoding such as CEA or prostate specific antigen (PSA) are also in clinical trials (J. L. Marshall et al., J. Clin. Oncol. 18:3964, 2000; M. Z. Zhu et al., Clin. Cancer Res. 6:24, 2000; I. M. Belyakov et al., Proc. Natl. Acad. Sci. USA 96:4512, 1999).

Tumor cell vaccines have also been based on tumor cells taken either from the patient being treated, or from an autologous source bearing a similar profile of tumor antigens. They are genetically modified to express a cytokine like GM-CSF or IL-4 that is thought to recruit the host immune system (J. W. Simons et al., Cancer Res. 59:5160, 1999; R. Soiffer et al., Proc. Natl. Acad. Sci. USA 95:13141, 1998; E. M. Jaffee et al., J. Clin. Oncol. 19:145, 2001; R. Salgia et al., J. Clin. Oncol. 21:624, 2003). Transfected tumor cell vaccines are in late-stage clinical trials for prostate cancer, lung cancer, pancreatic cancer, and leukemia (R. Salgia et al., J. Clin. Oncol. 21:624, 2003; K. M. Hege et al., Lung Cancer 41:S103, 2003).

An improved version of this approach is to isolate the patient's own tumor cells, and combine them with a cell line transfected to express a cytokine like GM-CSF in membranes form (U.S. Pat. No. 6,277,368). The transfected cells recruit the host immune system, which then initiates a CTL response against the tumor cells as bystanders. Another type of cellular vaccine comprises a patient's tumor cells combined with alloactivated T lymphocytes, which again play the role of recruiting the host immune system (U.S. Pat. Nos. 6,136,306; 6,203,787; and 6,207,147).

Because dendritic cells play a central role in presenting tumor antigen to prime the CTL compartment, there has been considerable research interest in autologous dendritic cells as a tumor vaccine (G. Schuler et al., Curr. Opin. Immunol. 15:138, 2003; J. A. Berzofsky et al., J. Clin. Invest. 113:1515, 2004). Clinical trials have been based on dendritic cells from two sources: a) purified DC precursors from peripheral blood (L. Fong & E. G. Engleman, Annu. Rev. Immunol. 15:138, 2003); and b) ex vivo differentiation of DCs from peripheral blood monocytes (F. Sallusto et al., J. Exp. Med. 179, 1109, 1994) or CD34+ hematopoietic progenitor cells (J. Banchereau et al., Cancer Res. 61:6451, 2001; A. Makensen et al., Int. J. Cancer 86:385, 2000).

D. Boczkowski et al. (J. Exp. Med. 184:465, 1996) reported that dendritic cells pulsed with RNA can act as antigen-presenting cells in vitro and in vivo. S. K. Nair et al. (Eur. J. Immunol. 27:589, 1997) reported that antigen-presenting cells pulsed with unfractionated tumor-derived peptides can act as tumor vaccines. F. O. Nestle et al. (Nat. Med. 4:328, 1998) reported vaccination of melanoma patients with peptide- or tumor lysate-pulsed dendritic cells. B. Thurner et al. (J. Exp. Med. 190:16169, 1999) reported vaccination with mage-3A1 peptide-pulsed dendritic cells in Stage IV melanoma. L. Fong et al. (J. Immunol. 167:7150, 2001) described dendritic cell-based xenoantigen vaccination for prostate cancer immunotherapy.

A. Heiser et al. (Cancer Res. 61:338, 2001; J. Immunol. 166:2953, 2001) reported that human dendritic cells transfected with renal tumor RNA stimulate polyclonal T cell responses against antigens expressed by primary and metastatic tumors. C. Milazzo et al. (Blood 101:977, 2002) reported the induction of myeloma-specific cytotoxic T cells using dendritic cells transfected with tumor-derived RNA. Z. Su et al., (Cancer Res. 63:2127, 2003) reported immunological and clinical responses in metastatic renal cancer patients vaccinated with tumor RNA-transfected dendritic cells.

Exosome-based immunotherapy has also recently attracted much attention, since tumor-derived exosomes are a rich source of shared tumor rejection antigens for CTL crosspriming. For immunotherapy, tumor exosomes are usually loaded onto dendritic cells before administering in vivo. Novel approaches to bypass antigen loading onto DC either in vivo or in vitro have been investigated; however, to date, there are no reports regarding the modification of exosomes themselves to improve the antitumor effect of exosome-based immunotherapy. While tumor exosomes appear to be enriched in potential antigenic targets, they also express immunosuppressive and apoptogenic activities. As a result, exosome-based immunotherapy for solid human cancers has exhibited at best marginal statistical success.

Unfortunately, few immunological treatments explored to date have achieved a high frequency of pathologically confirmed complete remissions, due in large part to the presence of an immunosuppressive tumor microenvironment. As such, although immunotherapies have the potential to specifically target and eliminate diseased tissues, including cancers, there is still an unmet need in the art for new immunotherapies that can overcome the immunosuppressive defenses of targeted tissues.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently-disclosed subject matter, an exosome isolated from a cell is provided. The exosome comprises one or more antigens and substantially lacks one or more immunosuppressive polypeptides normally found in the exosome. In some embodiments, the cell has been modified to inhibit expression of the one or more immunosuppressive polypeptides. In some embodiments, the exosome further comprises one or more exogenous antigens.

In some embodiments, the cell has been modified to comprise one or more inhibitory polynucleotides that specifically inhibit expression of the one or more immunosuppressive polypeptides. In some embodiments, the one or more inhibitory polynucleotides comprise siRNA polynucleotides.

In some embodiments, the cell is a cultured cell. In some embodiments, the cell is a cancer cell, such as for example, an ovarian cancer cell, a cervical cancer cell, a breast cancer cell, an endometrial cancer cell, a colon cancer cell, a prostate cancer cell, a lung cancer cell, a melanoma cell, or a pancreatic cancer cell. In some embodiments, the cell is a UL-1 cell, a UL-2, a UL-3 cell, or a UL-6 cell.

In some embodiments, the one or more antigens are cancer cell antigens. In some embodiments, the cancer cell antigen can be p53, p63, p73, mdm-2, procathepsin-D, B23, C23, PLAP, CA125, MUC-1, cerB/HER2, NY-ESO-1, SCP1, SSX-1, SSX-2, SSX-4, HSP27, HSP60, HSP90, GRP78, TAG72, HoxA7, HoxB7, EpCAM, ras, mesothelin, survivin, EGFK, MUC-1, or c-myc.

In some embodiments, the one or more immunosuppressive polypeptides are selected from the group consisting of FasL, programmed death ligand-1, programmed death ligand-2, B7-H3, B7-H4, and combinations thereof.

In some embodiments, the one or more exogenous antigens comprise superantigens. In some embodiments, the superantigens can be staphylococcal enterotoxins (SEs), a *Streptococcus pyogenes* exotoxin (SPE), a *Staphylococcus aureus* toxic shock-syndrome toxin (TSST-1), a streptococcal mitogenic exotoxin (SME) or a streptococcal superantigen (SSA).

In some embodiments of the presently-disclosed subject matter, a cell that produces the exosomes disclosed herein is provided.

In some embodiments of the presently-disclosed subject matter, a composition comprising an exosome disclosed herein and a pharmaceutical carrier is provided.

Further, the presently-disclosed subject matter provides in some embodiments, a method of producing an exosome disclosed herein substantially lacking one or more immunosuppressive polypeptides. In some embodiments, the method comprises providing a cell that can produce exosomes; inhibiting expression by the cell of one or more immunosuppressive polypeptides; and isolating exosomes produced by the cell, wherein the exosomes substantially lack the one or more immunosuppressive polypeptides. In some embodiments, the method further comprises decorating the exosomes with one or more exogenous antigens. In some embodiments of the method, isolating the exosomes comprises harvesting a media in which the cells are cultured.

Still further, in some embodiments of the presently-disclosed subject matter, a method of treating cancer in a subject is provided. In some embodiments, the method comprises administering an effective amount of an exosome disclosed herein, which is produced by a cancer cell, to a subject in need thereof. The exosome can comprise one or more cancer antigens and is substantially lack one or more immunosuppressive polypeptides. In some embodiments, the treated cancer is a solid tumor. In some embodiments, the treated cancer is an ovarian cancer cell, a cervical cancer cell, a breast cancer cell, an endometrial cancer cell, a colon cancer cell, a prostate cancer cell, a lung cancer cell, a melanoma cell, or a pancreatic cancer cell. In some embodiments, the exosome is administered intravenously, intratumorally, subcutaneously, transdermally, or intraperitoneally. In some embodiments, the exosome comprises one or more exogenous antigens, such as for example, superantigens. In some embodiments, the subject is a mammal.

Still further, in some embodiments of the presently-disclosed subject matter, a method of stimulating an immune response in a subject against one or more antigens is provided. In some embodiments, the method comprises administering an effective amount of an exosome disclosed herein, which is produced by a cell and comprising one or more antigens to a subject in need thereof. In some embodiments, the exosome is substantially lacking one or more immunosuppressive polypeptides.

Accordingly, it is an object of the presently disclosed subject matter to provide modified exosomes and methods of using the modified exosomes to treat disorders, including cancers. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, figures, and non-limiting examples.

DETAILED DESCRIPTION

Figure 1:
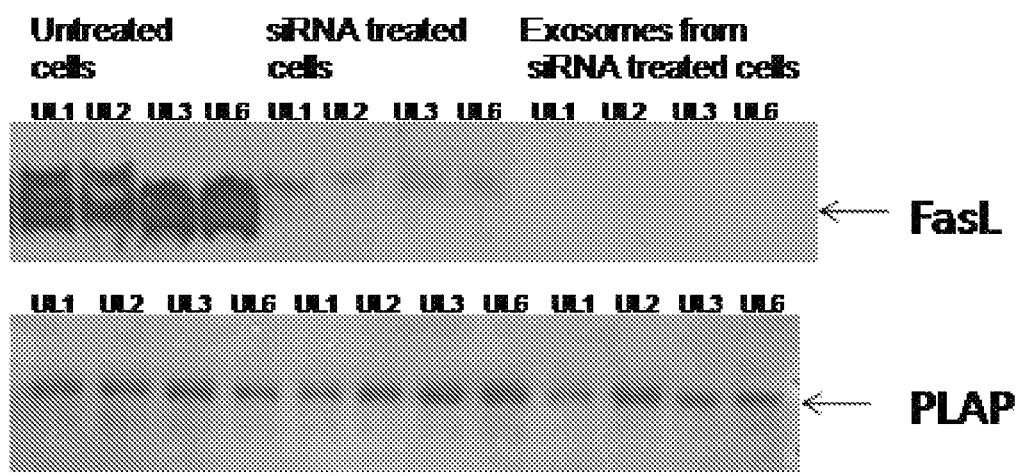
FIG. 1 is a photograph showing the expression of Fas ligand (FasL) by four (4) ovarian tumor cell lines (UL1, UL2, UL3, and UL6). Cell lines were either treated with mock siRNA or treated with siRNA primers specific for FasL. The expression of FasL was also assayed in expression of FasL on tumor-derived exosomes from siRNA treated cells. The levels of placental alkaline phosphatase (PLAP) was determined as a control for unaffected proteins. The gels define expression by western immunoblotting.

The details of one or more embodiments of the presently disclosed subject matter are set forth in the accompanying description below. Other features, objects, and advantages of the presently disclosed subject matter will be apparent from the detailed description, figures, and claims. All publications, patent applications, patents, and other references mentioned herein are incorporated by reference in their entirety. Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

Following long-standing patent law convention, the terms "a", "an" and "the" mean "one or more" when used in this application, including in the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

A general characteristic of activated cell types, including lymphocytes, dendritic cells, and embryonic cells, is their ability to release vesicular membrane material (termed microvesicles or exosomes). The release of exosomes appears to be an important feature of intercellular communication. Exosomes from activated immune cells modulate lymphocyte and dendritic cell functions by eliciting "activation induced cell death" (AICD). Lymphocytes and dendritic cells appear to release exosomes following activation and these appear to play an essential role in immunoregulation, preventing of excessive immune responses, and the development of autoimmunity. Cancer cells have also been demonstrated to release exosomes. However, in contrast to immune cell exosomes, cancer cell exosomes may constitute a facsimile of the immune cell exosome pathway that can actually circumvent immunosurveillance and recognition of the tumor by the immune system through the inclusion of immunosuppressive polypeptides in the cancer cell exosomes. Production of exosomes by cancer cells may help to explain why many immunotherapies targeted to cancers have not been as therapeutically effective as desired. In particular, the presence of immunosuppressive polypeptides within cancer-derived exosomes can inhibit the effective use of immunotherapeutic exosome cancer treatments by dampening desired immune responses in subjects in need of treatment.

The presently-disclosed subject matter provides at least two innovative approaches to improving exosomes for use in a therapeutic tumor antigen delivery system. First, one or more immunosuppressive polypeptides can be suppressed from expression and/or removed from exosomes derived from cells, e.g., cancer cells. In some embodiments, siRNA suppression is utilized to reduce or eliminate expression of one or more tumor-derived immunosuppressive polypeptides. Second, exosomes of the presently-disclosed subject matter can be modified to comprise one or more exogenous antigens (e.g., "superantigens") to enhance T cell-stimulating activity of the exosomes. In some embodiments, protein transfer techniques can be utilized to introduce the exogenous antigens into the exosomes.

The use of siRNA suppression provides for the selective suppression of immunosuppressive polypeptides, while maintaining the tumor antigen-enriched nature of tumor exosomes. To further enhance the immunogenic character of tumor exosomes, protein transfer can be used to express target proteins (e.g., superantigens) onto the cell surface. For example, staphylococcal enterotoxin A (SEA) is a superantigen with potent T cell-stimulating activity, which forms complexes with DC MHC class II molecules. Previous studies have demonstrated that SEA-anchored tumor cells can induce an antitumor immune response. Since exosomes are tumor antigen-enriched microvesicles, exosomes are an optimal target for protein transfer.

The novel therapeutic exosomes disclosed herein combine target protein anchorage for enhanced immune system targeting and reduction or elimination of one or more immunosuppressive molecules, such as immunosuppressive polypeptides (e.g., by siRNA-suppression techniques), normally found in the naturally-produced exosomes. These novel immunotherapeutic exosomes provide optimal tools to induce regression of established tumors, as well as prevention of initial tumor development. Both CD4+ and CD8+ T cells have been shown to proliferate in response to SEA, resulting in increased production of cytokines such as IFN-γ and IL-2. The use of cancer antigen-rich exosomes further provides the specificity necessary for an efficient therapy. The presently-disclosed tumor-derived exosomes surface anchored with exogenous superantigens and modified to lack immunosuppressive polypeptides can induce Th1 responses and tumor-specific CTL's more efficiently than any current approach.

As such, in some embodiments of the presently disclosed subject matter, an exosome isolated from a cell that produces the exosome is provided. In some embodiments, the exosome comprises one or more antigens of interest and substantially lacks one or more immunosuppressive molecules that would otherwise be found in the exosome, including on the surface of the exosome, when produced by the cell. In some embodiments, the immunosuppressive molecule is an miRNA or a polypeptide.

The term "isolated", when used in the context of an isolated DNA molecule or an isolated polypeptide, is a DNA molecule or polypeptide that, by the hand of man, exists apart from its native environment and is therefore not a product of nature. An isolated DNA molecule or polypeptide can exist in a purified form or can exist in a non-native environment such as, for example, in a transgenic host cell.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

Exosomes are vesicles of endosomal origin that are secreted in the extracellular milieu following fusion of late endosomal multivesicular bodies with the plasma membrane. Cells from various tissue types have been shown to secrete exosomes, such as dendritic cells, B lymphocytes, tumor cells and mast cells, for instance. Exosomes from different origins exhibit discrete sets of proteins and lipid moieties. They notably contain proteins involved in antigen presentation and immunomodulation, suggesting that exosomes play a role in cell-cell communications leading to the modulation of immune responses. Indeed, exosomes from dendritic cells (DC) pulsed with peptides derived from tumor antigens elicit anti-tumor responses in animal model using the matching tumor. However, exosomes derived from cancer cells comprising cancer antigens have been shown to comprise immunosuppressive polypeptides, making unmodified tumor-derived exosomes undesirable and potentially unsafe for use directly in vaccines.

The exosomes of the presently disclosed subject matter are well-suited for producing antigens that can stimulate desirable immune responses in subjects because they are produced by cells, rather than artificially-synthesized, and therefore provide antigens that are "natural". That is, the antigens produced by the cells and found in the exosome can be full-length peptides that are processed (e.g., glycosylated, etc.) and folded by the cell to a similar extent as antigens experienced by immune cells in a subject. As such, the exosome antigens can be utilized in vaccines or treatments against, for example cancers. In some embodiments, therefore, the one or more antigens can each comprise a cancer cell antigen. As non-limiting examples, the cancer cell antigen can be placental type alkaline phosphatase, p53, p63, p73, mdm-2, procathepsin-D, B23, C23, PLAP, CA125, MUC-1, cerB/HER2, NY-ESO-1, SCP1, SSX-1, SSX-2, SSX-4, HSP27, HSP60, HSP90, GRP78, TAG72, HoxA7, HoxB7, EpCAM, ras, mesothelin, survivin, EGFK, MUC-1, and c-myc.

As noted, in some embodiments, the exosomes are modified such that they substantially lack one or more immunosuppressive molecules, such as miRNAs or immunosuppressive polypeptides. An "immunosuppressive polypeptide" is a polypeptide that reduces a normal immunological reaction by an immune system in a subject to a particular antigen. For example, it has been demonstrated that exosomes released by tumor cells can suppress immune responses in a subject and can induce apoptosis in lymphocytes due to the presence of immunosuppressive molecules in the exosomes, including immunosuppressive polypeptides. See Taylor & Gercel-Taylor (*British Journal of Cancer* (2005) 92:305-311, herein incorporated by reference in its entirety). Exemplary "immunosuppressive molecules" include, but are not limited to, microRNAs and immunosuppressive polypeptides, such as for example FasL, programmed death ligand-1, programmed death ligand-2, B7-H3, B7-H4, and combinations thereof.

The term "substantially lacking", as used herein and with regard to immunosuppressive molecules, refers to the selective removal of substantially all or at least a significant proportion of one or more immunosuppressive molecules resulting in an exosome that is significantly reduced or substantially lacking one or more selected immunosuppressive molecules. The term "significantly reduced" refers to a result that is reduced by more than the margin of error inherent in the measurement technique when comparing the modified exosome to a similar exosome produced by a comparable cell under otherwise comparable conditions. In some embodiments a decrease in presence in the modified exosome of a particular selected immunosuppressive molecule by about 10% or greater over a baseline presence. In some embodiments a decrease in activation or activity by about 20% or greater, in some embodiments a decrease in activation or activity by about 25% or greater, and in some embodiments a decrease in activation or activity by about 50% or greater is a significantly reduced presence of the immunosuppressive molecule. In some embodiments, an exosome that is substantially lacking in one or more selected immunosuppressive molecules exhibits measurably reduced (as compared to the immunosuppressive capability of a comparable unmodified exosome) or absent capability to suppress one or more components of an animal immune system. Immunosuppressive capability of exosomes can be measured using any of several in vitro and in vivo assays generally known in the art. For example, and as described in detail in the Examples, expression of specific proteins associated with T cell activation can be measured and correlated with immunosuppressive activity (or lack thereof) in exosomes co-incubated with the T cells.

In some embodiments of the presently disclosed subject matter, the exosome further comprises one or more exogenous antigens. An "exogenous antigen", as the term is used herein, refers to an antigenic polypeptide that is not typically coded for and/or expressed in the exosome-producing cell, is therefore not a native polypeptide of the cell or exosome and so is typically not found in exosomes produced by the cell. The term "native" refers to a polypeptide that is encoded by a native gene of an untransformed cell's genome and is therefore naturally present in the cell when expressed.

Exogenous polypeptides can be included in the exosomes by a variety of techniques known in the art. For example, exogenous polypeptides can be decorated on the surface of the exosomes after they are excreted by the cells using protein transfer techniques generally known to those of skill in the art. See, e.g., Nagarajan S, Selvaraj P. Glycolipid-anchored IL-12 expressed on tumor cell surface induces antitumor immune response. Cancer Res 2002; 62:2869-74; McHugh R S, Nagarajan S, Wang Y, Sell K W, Selvaraj P. Protein transfer of glycosyl-phosphatidylinositol-B7-1 into tumor cell membranes: a novel approach to tumor immunotherapy. Cancer Res 1999; 59:2433-7; and Huang C, Yu H, Wang Q, Yang G, Ma W, Xia D, Chen X, Yi P, Shen F, Zheng H, Cao X. A novel antitumor approach: SEA-anchored tumor cells expressing heat shock protein 70 onto the surface elicit strong antitumor efficacy. Immonol Lett 2005; 101:71-80.

In addition, exogenous polypeptides can be incorporated into exosomes using recombinant expression techniques. Recombinant exosomes have been described in the art, which derive from cells transfected with plasmids encoding the recombinant polypeptides. Such recombinant exosomes contain the plasmid-encoded recombinant peptide (see e.g., PCT Published Application No. WO00/28001, herein incorporated by reference).

Exogenous polypeptides that can be incorporated into exosomes of the present subject matter are polypeptides that can provide additional desirable functionality to the exosomes, such as for example polypeptides that provide increased immunogenic properties to the exosomes. For example, in some embodiments, "superantigens" (SAgs) can be incorporated into the exosomes.

SAgs can comprise a group of bacterial and viral proteins that are extremely efficient in activating a large fraction of the T-cell population. SAgs can bind directly to the major histocompatibility complex (MHC) without being processed. In fact, SAgs can bind unprocessed outside the antigen-binding groove on the MHC class II molecules, thereby avoiding most of the polymorphism in the conventional peptide-binding site. The mechanism of binding depends on the SAgs binding to the T-cell receptor (TCR) in the Vβ chain, instead of binding to the hypervariable loops of the T-cell receptor (TCR).

Examples of superantigens that can be incorporated into exosomes as exogenous polypeptides include, but are not limited to staphylococcal enterotoxins (SEs), a *Streptococcus pyogenes* exotoxin (SPE), a *Staphylococcus aureus* toxic shock-syndrome toxin (TSST-1), a streptococcal mitogenic exotoxin (SME) and a streptococcal superantigen (SSA). SEs are a homologous group of superantigens, with regard to both structure and function. In specific embodiments, the exogenous polypeptide is staphylococcal enterotoxin A (SEA) or staphylococcal enterotoxin E (SEE). See, e.g., GENBANK® Accession Numbers AY291443 to AY291450 and B R Singh and M J Betley. Comparative structural analysis of staphylococcal enterotoxins A and E. J Biol Chem, 264, 4404-4411, 1989.), and the table following.

cancer cell, a colon cancer cell, a prostate cancer cell, a lung cancer cell, a melanoma cell, or a pancreatic cancer cell. In particular embodiments, the cell is a cultured cell line selected from the group consisting of a UL-1 cell, UL-2 cell, a UL-3 cell, and UL-6. All of these primary human ovarian tumor cell lines were established in our laboratory, from women with Stage IIIc cyst adenocarcinoma of the ovary (designated UL-1, UL-2, UL-3, and UL-6). UL-2 and UL-3 were derived from hereditary ovarian cancer, while UL-1 and UL-6 were derived from spontaneous cancers. UL-1 cells were derived from a 63 year old female, UL-2 cells were derived from a 34 year old female, UL-3 cells were derived from a 42 year old female, and UL-6 cells were derived from a 72 year old female patient. These cell lines are tumorigenic in nude mice, giving rise to tumors that are consistent with cyst adenocarcinomas. These cell lines are all positive for EpCAM, PLAP, FasL PD-L1 and class II MHC. For additional disclosure of these exemplary cell lines, see Gibb, R. K., et al. Apoptosis as a measure of chemosensitivity to cisplatin and Taxol therapy in ovarian cancer cell lines. Gynecologic Oncology, 65: 13-22, 1997; Chinni et al. Cathepsin D and glucose-regulated protein 78 recognized by the humoral response of ovarian cancer patients. Clinical Cancer Research, 3: 1557-1564, 1997; Bazzett et al. Modulation of proliferation and chemosensitivity by procathepsin D in ovarian cancer. Gynecologic Oncology, 74: 181-187, 1999; and Makhija et al. Regulation of chemotherapy induced apoptosis in ovarian cancer cell spheroids. International Journal of Oncology, 14: 515-521, 1999; each of which is herein incorporated by reference.

In some embodiments of the presently disclosed subject matter, a pharmaceutical composition is provided comprising an exosome disclosed herein and a pharmaceutical carrier. In some embodiment, the pharmaceutical composition is pharmaceutically acceptable in humans. The pharmaceutical composition can be formulated as a therapeutic composition for delivery to a subject in some embodiments.

A pharmaceutical composition as described herein preferably comprises a composition that includes pharmaceutical carrier such as aqueous and non-aqueous sterile injection solutions that can contain antioxidants, buffers, bacteriostats,

| Domain Info | Class | Fold | Superfamily | Family | Domain | Species |
| --- | --- | --- | --- | --- | --- | --- |
| d1esfa1 | All beta proteins | OB-fold | Bacterial enterotoxins | Superantigen toxins, N-terminal domain | Staphylococcal enterotoxin A, SEA | *Staphylococcus aureus* |
| d1esfb1 | All beta proteins | OB-fold | Bacterial enterotoxins | Superantigen toxins, N-terminal domain | Staphylococcal enterotoxin A, SEA | *Staphylococcus aureus* |
| d1esfa2 | Alpha and beta proteins (a + b) | beta-Grasp (ubiquitin-like) | Superantigen toxins, C-terminal domain | Superantigen toxins, C-terminal domain | Staphylococcal enterotoxin A, SEA | *Staphylococcus aureus* |
| d1esfb2 | Alpha and beta proteins (a + b) | beta-Grasp (ubiquitin-like) | Superantigen toxins, C-terminal domain | Superantigen toxins, C-terminal domain | Staphylococcal enterotoxin A, SEA | *Staphylococcus aureus* |

In some embodiments of the presently disclosed subject matter, a cell that produces the exosomes disclosed herein is provided. In some embodiments, the cell is a cultured cell, that is, a cell propagated ex vivo in culture media. The culture cell can be immortalized to facilitate continuous propagation. In some embodiments, the cell is a cancer cell, such as for example a cancer cell originally isolated from a tumor and then propagated in culture, as is generally known in the art. In some embodiments, the cancer cell can be an ovarian cancer cell, a cervical cancer cell, a breast cancer cell, an endometrial bactericidal antibiotics and solutes that render the formulation isotonic with the bodily fluids of the intended recipient; and aqueous and non-aqueous sterile suspensions, which can include suspending agents and thickening agents.

The pharmaceutical compositions used can take such forms as suspensions, solutions or emulsions in oily or aqueous vehicles, and can contain formulatory agents such as suspending, stabilizing and/or dispersing agents.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

In addition to the exosomes comprising one or more antigens and exogenous peptides within the exosomes, other components, such as a vehicle for exosome delivery and additional immunostimulatory substances within the vehicle designed to enhance the polypeptide's immunogenicity can be included in the pharmaceutical composition. The immunogenic compositions and vaccines according to the presently disclosed subject matter can further comprise or consist essentially of one or more adjuvants. Suitable adjuvants for use in the practice of the present subject matter include, but are not limited to (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman et al., Proc. Natl. Acad. Sci., USA, 1996, 93, 2879-2883; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof.

The oil in water emulsion (3) can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil can be used in combination with emulsifiers to form an emulsion. The emulsifiers can be nonionic surfactants, such as: esters of, on the one hand, sorbitan, mannide (e.g. anhydromannitol oleate), glycerol, polyglycerol or propylene glycol and, on the other hand, oleic, isostearic, ricinoleic or hydroxystearic acids, the esters being optionally ethoxylated, or polyoxypropylene-polyoxyethylene copolymer blocks, such as Pluronic, e.g., L121.

Among the type (1) adjuvant polymers, preference is given to polymers of cross-linked acrylic or methacrylic acid, especially cross-linked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers cross-linked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name CARBOPOL™ (BF Goodrich, Ohio, U.S.A.) can be suitable. They are cross-linked by allyl saccharose or by allyl pentaerythritol. Among them, reference is made to CARBOPOL™ 974P, 934P and 971 P.

As to the maleic anhydride-alkenyl derivative copolymers, EMA (Monsanto, St. Louis, Mo., U.S.A.) can be utilized, which are straight-chain or cross-linked ethylene-maleic anhydride copolymers and they are, for example, cross-linked by divinyl ether. Reference is also made to J. Fields et al., *Nature* 186: 778-780, Jun. 4, 1960.

The presently disclosed subject matter further provides methods of using the exosomes disclosed herein. In some embodiments, a method of producing an exosome substantially lacking one or more immunosuppressive polypeptides is provided. In some embodiments, the method comprises providing a cell, such as the cells disclosed hereinabove, that can produce exosomes; inhibiting expression by the cell of one or more immunosuppressive polypeptides; and isolating exosomes produced by the cell, wherein the exosomes substantially lack the one or more immunosuppressive polypeptides.

In some embodiments, the method can further comprise stimulating the cell to produce the exosomes. However, in cancer cells and other cell types that naturally produce exosomes, stimulation is generally not required.

In some embodiments, the method further comprises decorating the exosomes (e.g., by protein transfer or by recombinant expression in the cells producing the exosomes, as disclosed herein and as is generally known in the art) with one or more exogenous antigens (e.g., superantigens).

In some embodiments, "isolating the exosomes" comprises harvesting a media in which the cells are cultured and selectively removing the exosomes from the media, such as for example by centrifugation.

In some embodiments of the method, inhibiting expression by the cell of the one or more immunosuppressive polypeptides comprises introducing into the cell one or more inhibitory polynucleotides that specifically inhibit expression of the one or more immunosuppressive polypeptides. In some embodiments, the one or more inhibitory polynucleotides comprise small interfering RNA (siRNA) polynucleotides.

The terms "nucleic acid" and "polynucleic acid" refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res* 19:5081; Ohtsuka et al. (1985) *J Biol Chem* 260:2605-2608; Rossolini et al. (1994) *Mol Cell Probes* 8:91-98). The terms "nucleic acid", "polynucleotide", or "nucleic acid sequence" can also be used interchangeably with gene, open reading frame (ORF), cDNA, and mRNA encoded by a gene.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, *Nature* 411:428-429, 2001; Elbashir et al., *Nature* 411:494-498, 2001a; and PCT International Publication Nos. WO 00/44895, WO 01/36646, WO 99/32619, WO 00/01846, WO 01/29058, WO 99/07409, and WO 00/44914, each of which is herein incorporated by reference. In one embodiment, the siRNA comprises a double stranded polynucleotide molecule comprising complementary sense and antisense regions, wherein the antisense region comprises a sequence complementary to a region of a target nucleic acid molecule encoding an immunosuppressive polypeptide. In another embodiment, the siRNA comprises a single stranded polynucleotide having self-complementary sense and antisense regions, wherein the antisense region comprises a sequence complementary to a region of the target nucleic acid molecule. In another embodiment, the siRNA comprises a single stranded polynucleotide having one or more loop structures and a stem comprising self complementary sense and antisense regions, wherein the antisense region comprises a sequence complementary to a region of the target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See generally Fire et al., *Nature* 391:806-811, 1998. The process of post-transcriptional gene silencing is thought to be an evolutionarily conserved cellular defense mechanism that has evolved to prevent the expression of foreign genes (Fire, *Trends Genet* 15:358-363, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., *Nature* 409:363-366, 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., *Genes Dev* 15:188-200, 2001b).

RNAi has been described in several cell types and organisms. Fire et al., 1998 described RNAi in *C. elegans*. Wianny & Zernicka-Goetz, *Nature Cell Biol* 2:70-75, 1999 disclose RNAi mediated by dsRNA in mouse embryos. Hammond et al., *Nature* 404:293-296, 2000 were able to induce RNAi in *Drosophila* cells by transfecting dsRNA into these cells. Elbashir et al. *Nature* 411:494-498, 2001 demonstrated the presence of RNAi in cultured mammalian cells including human embryonic kidney and HeLa cells by the introduction of duplexes of synthetic 21 nucleotide RNAs.

Other studies have indicated that a 5'-phosphate on the target-complementary strand of a siRNA duplex facilitate siRNA activity and that ATP is utilized to maintain the 5'-phosphate moiety on the siRNA (Nykanen et al., *Cell* 107: 309-321, 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359, 180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi), each of which is incorporated herein by reference.

In some embodiments, the presently disclosed subject matter utilizes RNAi to at least partially inhibit expression of one or more immunosuppressive polypeptides of interest, for example but not limited to, FasL, programmed death ligand-1, programmed death ligand-2, B7-H3, B7-H4, or combinations thereof. In some embodiments, inhibition is at least about 10% of normal expression amounts. In some embodiments, the method comprises introducing an RNA to a target cell in an amount sufficient to inhibit expression of the one or more immunosuppressive polypeptides, wherein the RNA comprises a ribonucleotide sequence which corresponds to a coding strand of a gene of interest.

The RNA can have a double-stranded region comprising a first strand comprising a ribonucleotide sequence that corresponds to the coding strand of the gene encoding the target immunosuppressive polypeptide and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases. See, e.g., Koyanagi et al. Long-term exposure to superantigen induces p27Kip1 and Bcl-2 expression in effector memory CD4+ T cells. Cellular Immunology, 248 (2):77-85, 2007 August; and Tritto et al. The acquired immune response to the mucosal adjuvant LTK63 imprints the mouse lung with a protective signature. Journal of Immunology, 179(8):5346-57, 2007 Oct. 15, each of which is herein incorporated by reference.

In some embodiments, a recombinant virus comprising nucleic acid encoding the RNA can be produced. Introducing the RNA into a target cell then comprises infecting the target cell with the recombinant virus. Cellular polymerases transcribe the RNA resulting in expression of the RNA within the target cell. Engineering recombinant viruses is well known to those having ordinary skill in the art. See, e.g., Tritto et al. The acquired immune response to the mucosal adjuvant LTK63 imprints the mouse lung with a protective signature. Journal of Immunology. 179(8):5346-57, 2007 Oct. 15, herein incorporated by reference. One of skill would readily appreciate the multiple factors involved in selecting the appropriate virus and vector components needed to optimize recombinant virus production for use with the presently disclosed subject matter without the necessity of further detailed discussion herein.

In some embodiments of the presently disclosed subject matter, a method of treating cancer in a subject is provided. In some embodiments, the method comprises administering an effective amount of an exosome produced by a cancer cell, such as cancer cells and exosomes disclosed herein, to a subject in need thereof, wherein the exosome comprises one or more cancer antigens and is substantially lacking one or more immunosuppressive polypeptides. The administered exosome can act as a "vaccine" with regard to the antigens provided on the exosomes and thereby promotes an immune response against the antigens by the subject's immune system. However, it should be noted that the term "vaccine" as used herein is not intended to limit the present subject matter to methods of preventing disorders only, but is inclusive of therapies for treating disorders already present in a subject.

The stimulated immune system is then capable of mounting a response against cells comprising the antigens, including for example cancer cells. As such, the presently disclosed subject matter further provides in some embodiments a method of stimulating an immune response in a subject against one or more antigens, comprising administering an effective amount of an exosome produced by a cell and comprising one or more antigens to a subject in need thereof, wherein the exosome is substantially lacking one or more immunosuppressive polypeptides.

As used herein, the terms "treatment" or "treating" relate to any treatment of a condition of interest (e.g., a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

The term "cancer" refers to all types of cancer or neoplasm or malignant tumors found in animals, including leukemias, carcinomas and sarcomas.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some particular embodiments, the treated cancer is a solid tumor. In some embodiments, the treated cancer is an ovarian cancer cell, a cervical cancer cell, a breast cancer cell, an endometrial cancer cell, colon cancer cell, a prostate cancer cell, a lung cancer cell, a melanoma cells, or a pancreatic cancer cell.

The term "effective amount" is used herein to refer to an amount of the therapeutic composition (e.g., a composition comprising an exosome disclosed herein) sufficient to produce a measurable biological response (e.g., an immune response (e.g., antibody production and/or T cell activation) by the subject against antigens contained on the exosome and/or a measurable decrease in tumor size, activity, etc.). Actual dosage levels of active ingredients in a therapeutic composition of the presently disclosed subject matter can be varied so as to administer an amount of the active compound (s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., (1966) *Cancer Chemother Rep.* 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. (Freireich et al., (1966) *Cancer Chemother Rep.* 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Administration may be, for example, intravenously, intratumorally, subcutaneously, transdermally, or intraperitoneally.

For parenteral administration, the exosomes can be employed in an amount ranging from about 0.005 mg/kg to about 100 mg/kg, preferably about 10 to 50 or 10 to 70 mg/kg, and more preferably from about 10 mg/kg to about 30 mg/kg.

For additional guidance regarding formulation and dose, see U.S. Pat. Nos. 5,326,902; 5,234,933; PCT International Publication No. WO 93/25521; Berkow et al., (1997) *The Merck Manual of Medical Information*, Home ed. Merck Research Laboratories, Whitehouse Station, N.J.; Goodman et at, (1996) *Goodman & Gilman's the Pharmacological Basis of Therapeutics*, 9th ed. McGraw-Hill Health Professions Division, New York; Ebadi, (1998) *CRC Desk Reference of Clinical Pharmacology*. CRC Press, Boca Raton, Fla.; Katzung, (2001) *Basic & Clinical Pharmacology*, 8th ed. Lange Medical Books/McGraw-Hill Medical Pub. Division, New York; Remington et al., (1975) *Remington's Pharmaceutical Sciences*, 15th ed. Mack Pub. Co., Easton, Pa.; and Speight et al., (1997) *Avery's Drug Treatment: A Guide to the Properties, Choice, Therapeutic Use and Economic Value of Drugs in Disease Management*, 4th ed. Adis International, Auckland/Philadelphia; Duch et al., (1998) *Toxicol. Lett.* 100-101:255-263.

Suitable methods for administering to a subject a composition comprising exosomes disclosed herein in accordance with the methods of the present subject matter include but are not limited to systemic administration, intravenous administration, intratumoral administration, intramuscular administration, intraarterial administration, intraperitoneal administration, subcutaneous administration, inhalation, intratracheal installation, surgical implantation, transdermal delivery, local injection, and hyper-velocity injection/bombardment. Where applicable, continuous infusion can enhance drug accumulation at a target site, if desired (see, e.g., U.S. Pat. No. 6,180,082).

The particular mode of drug administration used in accordance with the methods of the present subject matter depends on various factors, including but not limited to the particular exosome composition (e.g., antigen characteristics and concentration, presence of additional antigenic molecules such as SAgs, etc.), carrier employed, the severity of the condition to be treated, and mechanisms for metabolism or removal of the drug following administration.

Further with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

It will be understood that various details of the presently disclosed subject matter may be changed without departing from the scope of the present subject matter. Furthermore, the foregoing description is for the purpose of illustration only, and not for the purpose of limitation.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Suppression of Expression of Immunosuppressive Polypeptides in Tumor Cells using siRNA Specific siRNAs were used with tumor-derived cell cultures, which in this Example were ovarian cancer cells, to suppress the expression of immunosuppressive polypeptides normally expressed by the cultured cells on exosomes produced by the cells. As one example of the capabilities of the present system, we investigated Fas Ligand (FasL), which is known to be associated with tumor-derived exosomes. However, the present methodology can function equally well in the suppression of one or more other immunosuppressive polypeptides found on tumor-derived exosomes, including but not limited to programmed death ligand-1, programmed death ligand-2, B7-H3, and B7-H4.

Briefly, tumor-derived cells ($2 \times 10^5$ cells/well) were plated onto six-well tissue culture plates in 2 ml antibiotic-free Roswell Park Memorial Institute (RPMI) media supplemented with ultracentrifuged FBS. To subconfluent cell cultures, the siRNA duplex solution (2-8 µl of siRNA duplex: 0.25-1 µg siRNA into 100 µl siRNA Transfection Medium™ (Santa Cruz Biotechnology, Inc, Santa Cruz, Calif., cat no. sc-36868) was added directly to dilute Transfection Reagent (Santa Cruz Biotechnology, Inc, cat no. sc-29528). The cells were incubated for 18 hrs, the medium removed and replaced with complete medium with 10% ultracentrifuged FBS and 1× antibiotics. After 72 hours, the conditioned medium was removed and exosomes isolated.

Antibody and siRNA pairs are commercially available for the known immunosuppressive polypeptides. For example, the exemplary antibody and siRNAs utilized in the present examples were purchased from Santa Cruz Biotechnology, Inc, Santa Cruz, Calif. and are as follows:

| Protein | siRNA | Antibody |
|---------|----------|----------|
| FasL    | sc-29313 | sc-56099 |
| PD-L1   | sc-39699 | sc-19090 |
| PD-L2   | sc-39701 | sc-80285. |

Exosomes were isolated from the conditioned media of siRNA-treated tumor cells. Conditioned media from ovarian cancer cell lines were used to isolate the exosomes. The >500 kD material was concentrated by ultrafiltration and applied to a SEPHAROSE® 2B column (Sigma Chemical Co., St. Louis, Mo., U.S.A.). The $>5 \times 10^7$ Da material was subjected to floatation on a discontinuous sucrose gradient and the quantity of isolated exosomes determined by the Bradford microassay method (Bradford, A rapid and sensitive method for the quantitation of microgram quantities of protein utilizing the principle of protein-dye binding, Anal Biochem, 72, 248-254 (1976)).

Example 2

Isolation and Analysis of Modified Exosomes from siRNA Treated Cells

To confirm that the siRNA approach suppresses the expression of the specific protein(s) of interest within the cell and its presence on exosomes released by these cells, western immunoblot analyses of the cells and isolated exosomes was performed (FIG. 1). The blots were probed overnight at 4° C. with the specific antibody for the specific protein component modified and bound complexes were visualized by ECL and quantitated by densitometry. The western immunoblot analysis of siRNA treated cells confirmed the knockdown of FasL expression within the original tumor cells and the absence of FasL associated with exosomes derived from these treated cells.

Example 3

Correlate Loss of Specific Proteins with Suppression of Immunosuppressive Activities of Exosomes The effects of siRNA-modified exosomes on T cells and dendritic cells (DC) were analyzed using the unmodified exosomes. Jurkat E-61 cells, a human T-cell lymphoma with a functional TcR/CD3 complex capable of synthesizing IL-2 was obtained from the American Type Culture Collection (Rockville, Md.). These cells were utilized as an in vitro assay for lymphocyte modulation by ascites-derived MF. These T cell lines were grown in RPMI 1640 medium supplemented with 0.1 mM nonessential amino acids, 1 mM sodium pyruvate, 200 mM L-glutamate, 100 µg/ml streptomycin and 100 IU/ml penicillin in a humidified 5% $CO_2$ chamber at 37° C. Cell viability was evaluated by trypan blue exclusion. All cultures utilized for this study were >95% viable.

For bioassay of CD3-zeta and JAK3 expressions, viable Jurkat cells ($10^6$ cells/ml) were incubated in a medium supplemented with 400 µg/ml isolated exosomes, modified with siRNA or unmodified, for 4 days and were compared with unexposed Jurkat cells or Jurkat cells exposed to the analogous chromatographic fractions from control sera. After 4 days, the cells were centrifuged, the cell pellet washed, and used for either protein or mRNA analysis.

Figure 2:
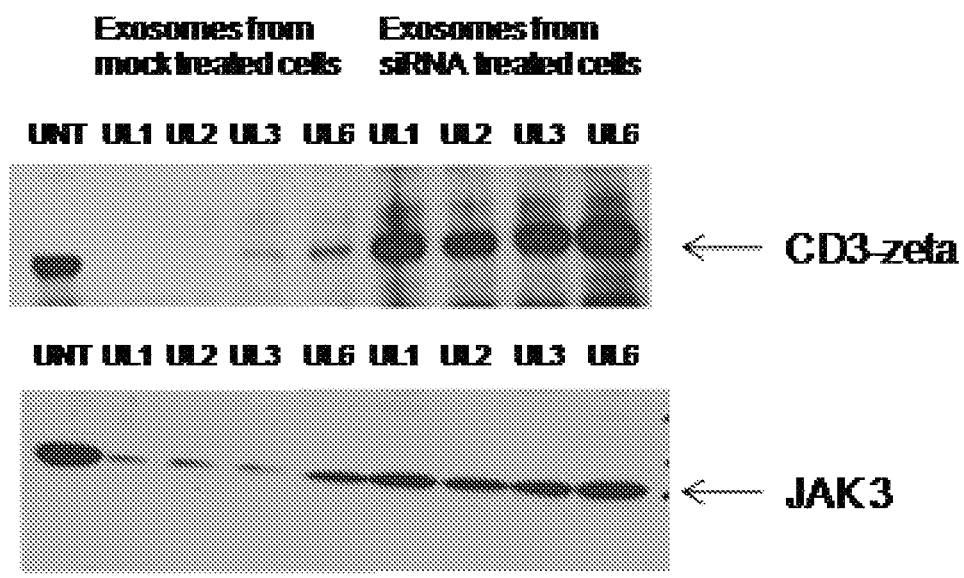
FIG. 2 is a pair of photographs of gels showing the consequences of co-incubated tumor-derived exosomes with T cells on the expression of the essential activation signal transducing proteins, CD3zeta and JAK3. The gels define the expression of the signaling molecules by western immunoblotting.

To assess CD3-zeta protein, the cell pellet was lysed using 50 mM HEPES, pH7.2, 150 mM NaCl, 5 mM EDTA, 1 mM sodium orthovanadate, 2.5% Triton X-100, 200 µg/ml trypsin/chymotrypsin inhibitor, 200 µg/ml chymostatin and 2 mM PMSF. The cell lysate was assayed for protein by the BioRad protein assay (Bio-Rad Laboratories, Hercules, Calif.). The modulation of CD3-zeta was analyzed by western immunoblot using a 15% SDS-PAGE gel, as described above with mouse monoclonal anti-CD3-zeta and rabbit polyclonal anti-JAK3 antibody (Santa Cruz Biotechnology, Santa Cruz, Calif.) as the primary antibody (FIG. 2).

Exosomes derived from tumor cell cultures treated with siRNA for FasL and thus not expressing FasL failed to inhibit the expressions of CD3-zeta or JAK3 within the T cell cultures. Since the suppression of CD3-zeta and JAK3 have been correlated with the presence of ovarian cancer, the extent of disease, and overall patient survival, the reversal of this exosome-derived suppression can result in increased patient T cell responses and improved patient survival.

Example 4

Protein Transfer of SEA-TM onto Exosomes and Their Confirmation

For incorporation of SEA to the exosome surface, exosomes can be isolated from B16-F10 cells, which will suppress T cell activation. The exosomal FasL1 expression can be modified by treatment of the B16-F10 cells with siRNA from FasL. The modified exosomes can be labeled with SEA.

Briefly, 100 µl of SEA (50 µg/ml) can be added to the 100 µg isolated modified exosomes in 100 µl phosphate-buffered saline (PBS). This solution can be incubated for 20 min at 37° C. and then PBS to a final volume of 1 ml. Unincorporated SEA can be removed with by chromatographing on Sepharose 2B.

Example 5

Immunizations and Tumor Challenge

C57BL/6 mice can be immunized sc with 10 µg exosome/SEA complex, three times at 7-day intervals. B16-F10 cells ($1\times10^5$) can then be injected sc, 1 week after the last injection. The tumor sizes can be measured every 2 days, and the long-term survival was observed daily up to 90 days. Mice can be euthanized when tumors reached 3 cm in diameter. Each group can contain 10 mice, for example.

Example 6

T Cell Proliferation and Cytokine Secretion In Vitro

To define the activity of the modified exosomes, 1 week after the last immunization, the splenic T cells can be isolated using pan-T-cell magnetic beads to 95% purity as confirmed by flow cytometry. These CD3+ T cells, $1\times10^5$, obtained from treated mice can be co-incubated with $2\times10^4$ inactivated B16-F10 cells (inactivated by treatment with 50 μg/ml mitomycin C) in 96-well plates for 5 days. T-cell proliferation can be determined after 72 hours using the CellTiter Aqueous cell proliferation assay (Promega).

Example 7

Elispot Assay for IFN-γ

To assess immunologic activity, the production of IFN-γ can be defined. For IFN-γ enzyme-linked immunospot (ELISPOT) assay, 7 days after the last immunization, splenocytes can be isolated and assayed at $5\times10^6$/ml. The lymphocytes can be stimulated with 10 μg/ml of the labeled, modified exosomes versus unlabeled, unmodified exosomes or 5 μg/ml Concanavalin A for 3 days. The treated lymphocytes will be transferred to the ELISPOT plate, and the IFN-γ-specific secreting colonies will be counted using a dissecting microscope.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. An exosome isolated from a cancer cell modified to substantially lack expression of one or more immunosuppressive polypeptides, wherein the exosome is substantially lacking the one or more immunosuppressive polypeptides and wherein the one or more immunosuppressive polypeptides are selected from the group consisting of FasL, programmed death ligand-I, programmed death ligand-2, B7-H3, B7-H4, and combinations thereof.

2. The exosome of claim 1, wherein the cell has been modified to comprise one or more inhibitory polynucleotides that specifically inhibit expression of the one or more immunosuppressive polypeptides.

3. The exosome of claim 2, wherein the one or more inhibitory polynucleotides comprise siRNA polynucleotides.

4. The exosome of any one of claim 1, wherein the cell is a cultured cell.

5. The exosome of claim 1, wherein the cancer cell is an ovarian cancer cell, a cervical cancer cell, a breast cancer cell, an endometrial cancer cell, a colon cancer cell, a prostate cancer cell, a lung cancer cell, a melanoma cell, or a pancreatic cancer cell.

6. The exosome of claim 1, wherein the cell is a UL-1 cell, a UL-2, a UL-3 cell or a UL-6 cell.

7. The exosome of claim 1, wherein the exosome comprises one or more cancer cell antigens.

8. The exosome of claim 7, wherein the cancer cell antigen is selected from the group consisting of p53, p63, p'73, mdm- 2, procathepsin-D, B23, C23, PLAP, CA125, MUC-1, cerB/ HER2, NY-ESO-1, SCP1, SSX-1, SSX-2, SSX-4, HSP27, HSP60, HSP90, GRP78, TAG72, HoxA7, HoxB7, EpCAM, ras, mesothelin, survivin, EGFK, MUC-1, and c-myc.

9. The exosome of claim 1, comprising one or more exogenous antigens.

10. The exosome of claim 9, wherein the one or more exogenous antigens comprise superantigens.

11. The exosome of claim 9, wherein the superantigen comprises staphylococcal enterotoxins (SEs), a *Streptococcus pyogenes* exotoxin (SPE), a *Staphylococcus aureus* toxic shock-syndrome toxin (TSST-1), a streptococcal mitogenic exotoxin (SME), or a streptococcal superantigen (SSA).

12. A cell that produces the exosome of claim 1.

13. The cell of claim 12, wherein the cell is a cultured cell.

14. The cell of claim 12, wherein the cell is a cancer cell.

15. The cell of claim 14, wherein the cancer cell is an ovarian cancer cell, a cervical cancer cell, a breast cancer cell, an endometrial cancer cell, a colon cancer cell, a prostate cancer cell, a lung cancer cell, a melanoma cell, or a pancreatic cancer cell.

16. The cell of claim 15, wherein the cell is a UL-3 cell, UL-2, or a UL-6 cell.

17. A composition, comprising: (a) an exosome of claim 1; and (b) a pharmaceutical carrier.

18. The exosome of claim 7, wherein the cancer cell is an ovarian cancer cell, a cervical cancer cell, a breast cancer cell, an endometrial cancer cell, a colon cancer cell, a prostate cancer cell, a lung cancer cell, a melanoma cell, or a pancreatic cancer cell.

19. The exosome of claim 8, wherein the cancer cell is an ovarian cancer cell, a cervical cancer cell, a breast cancer cell, an endometrial cancer cell, a colon cancer cell, a prostate cancer cell, a lung cancer cell, a melanoma cell, or a pancreatic cancer cell.

20. The exosome of claim 11, wherein the cancer cell is an ovarian cancer cell, a cervical cancer cell, a breast cancer cell, an endometrial cancer cell, a colon cancer cell, a prostate cancer cell, a lung cancer cell, a melanoma cell, or a pancreatic cancer cell.

21. The exosome of claim 7, wherein the cancer cell is an ovarian cancer cell.

22. The exosome of claim 8, wherein the cancer cell is an ovarian cancer cell.

23. The exosome of claim 11, wherein the cancer cell is an ovarian cancer cell.

24. The exosome of claim 1, wherein the modification to substantially lack expression of the one or more immunosuppressive polypeptides is attained by inhibiting transcription, inhibiting translation, or protein degradation of the one or more immunosuppressive polypeptides.

* * * * *

UNITED STATES PATENT AND TRADEMARK OFFICE
CERTIFICATE OF CORRECTION

PATENT NO. : 8,455,188 B2
APPLICATION NO. : 12/524432
DATED : June 4, 2013
INVENTOR(S) : Taylor et al.

It is certified that error appears in the above-identified patent and that said Letters Patent is hereby corrected as shown below:

In the claims:

In claim 1, col. 22, line 47: delete "ligand-I" and replace with "ligand-1"

In claim 4, col. 22, line 55: delete "any one of"

Signed and Sealed this
Twenty-third Day of July, 2013

Teresa Stanek Rea
*Acting Director of the United States Patent and Trademark Office*